(12) United States Patent
Fanselow et al.

(10) Patent No.: US 8,721,795 B2
(45) Date of Patent: *May 13, 2014

(54) CONVERSION METHOD

(75) Inventors: Markus Fanselow, Belfast (GB); John Holbrey, Belfast (GB); Kenneth Richard Seddon, Belfast (GB); Laurent Vanoye, Belfast (GB); Anna Zheng, Belfast (GB)

(73) Assignee: Petroliam Nasional Berhad (PETRONAS), Kuala Lumpar (MY)

( * ) Notice: Subject to any disclaimer, the term of this patent is extended or adjusted under 35 U.S.C. 154(b) by 738 days.

This patent is subject to a terminal disclaimer.

(21) Appl. No.: 12/676,824

(22) PCT Filed: Sep. 3, 2008
(Under 37 CFR 1.47)

(86) PCT No.: PCT/GB2008/050779
§ 371 (c)(1),
(2), (4) Date: Jan. 7, 2011

(87) PCT Pub. No.: WO2009/030949
PCT Pub. Date: Mar. 12, 2009

(65) Prior Publication Data
US 2011/0312048 A1    Dec. 22, 2011

(30) Foreign Application Priority Data
Sep. 6, 2007 (EP) .................................... 07253518

(51) Int. Cl.
*C13K 1/02* (2006.01)
(52) U.S. Cl.
USPC .......................................................... 127/37

(58) Field of Classification Search
USPC .......................................................... 127/37
See application file for complete search history.

(56) References Cited

U.S. PATENT DOCUMENTS

| 6,824,599 B2 | 11/2004 | Swatloski et al. |
| 2003/0157351 A1 | 8/2003 | Swatloski et al. |

FOREIGN PATENT DOCUMENTS

| CN | 101289817 A | 10/2008 |
| DE | 10 2004 031 025 | 12/2005 |
| EP | 1 860 201 | 11/2007 |
| WO | WO 2005/017001 | 2/2005 |
| WO | WO 2007/101811 | 9/2007 |
| WO | WO 2007/101812 | 9/2007 |

OTHER PUBLICATIONS

Badger et al. "Ethanol From Cellulose: A General Review." *Trends in new crops & new uses.* 2002. pp. 17-21.
Gesch et al. "Cuphea Growth and Development: Responses to Temperature." *Trends in New Crops and New Uses.* 2001. pp. 213-215.

*Primary Examiner* — Elvis O Price
(74) *Attorney, Agent, or Firm* — Merchant & Gould P.C.

(57) ABSTRACT

A process is described for the preparation of water-soluble cellulose hydrolysis products The process comprises admixing cellulose with an ionic liquid capable of solvating or dissolving at least some of the cellulose, said ionic liquid being a compound comprised solely of cations and anions and which exists in a liquid state at a temperature at or below 150° C., and in which the anions are selected from sulfate, hydrogen sulfate and nitrate; and treating the resulting solvate or solution with an acid in the presence of water, said acid having a pKa in water of less than 2 at 25° C.

18 Claims, No Drawings

CONVERSION METHOD

This application is a National Stage Application of PCT/GB2008/050779, filed 3 Sep. 2008, which claims benefit of Ser. No. 07253518.0, filed 6 Sep. 2007 in Europe and which applications are incorporated herein by reference. To the extent appropriate, a claim of priority is made to each of the above disclosed applications.

The present invention relates to a method of hydrolysing cellulose to generate water soluble monosaccharide, disaccharide and oligosaccharide derivatives thereof.

Cellulose is the most abundant biorenewable material on earth. Cellulose consists of polydisperse linear polymeric chains formed by repeated connection of beta-D-glucose building blocks through a 1-4 glycosidic linkage. These linear polymer chains form hydrogen-bonded supramolecular structures that are insoluble in water and most common organic solvents. It is known that hydrolysis of cellulose generates monosaccharide, disaccharide and oligosaccharide products, with glucose usually being the main hydrolysis product. Such products are capable of being fermented to generate alcohols for use as a fuel or a component of a fuel.

cellulose can be dissolved in a hydrophilic ionic liquid in the substantial absence of water or a nitrogen-containing base to form an admixture, which is then agitated until dissolution is complete, while WO 2005/017001 discloses that wood, straw and other natural lignocellulosic materials can be dissolved in certain ionic liquids under microwave irradiation and/or under pressure. The present inventors have now found that certain ionic liquids containing a certain specific anion can be used in a process for the hydrolysis of cellulose.

Accordingly, the present invention provides a process for the preparation of water-soluble cellulose hydrolysis products, which comprises admixing cellulose with an ionic liquid capable of solvating or dissolving at least some of the cellulose, said ionic liquid being a compound comprised solely of cations and anions and which exists in a liquid state at a temperature at or below 150° C., and in which the anions are selected from sulfate, hydrogen sulfate and nitrate; and treating the resulting solvate or solution with an acid in the presence of water, said acid having a pKa in water of less than 2 at 25° C.

Throughout this specification and claims, except where the context requires otherwise, the term "cellulose" should be

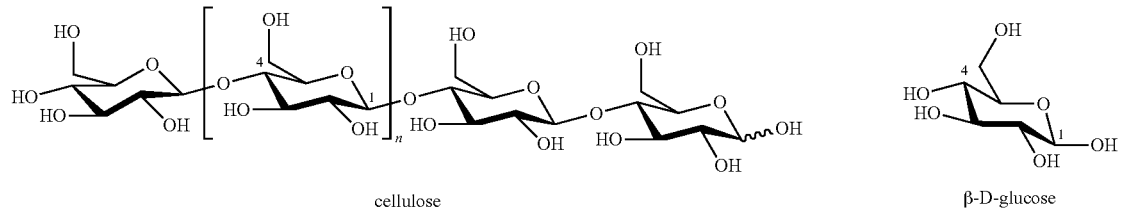

cellulose                                                                 β-D-glucose Glucose in particular is an important intermediate for fermentation to ethanol and other chemicals; therefore, saccharification of cellulose is of interest in the development of biofuels.

Chemical, enzymatic, microbiological and macrobiological catalysts can be used to accelerate the hydrolysis of cellulose under conditions selected to be thermodynamically favourable to product formation. Chemical and enzymatic hydrolysis of cellulose is discussed in "The Encyclopaedia of Polymer Science and Technology", 2nd Ed, J. I. Kroschwitz (Ed in Chief), Wiley (New York), 1985. Thus, cellulose may be hydrolysed using cellulolytic enzymes (cellulase) or harvested filamentous fungi such as *Trichoderma* sp. However, hydrolysing cellulose by chemical methods presents many problems. In general, such methods have involved one of two approaches: dilute acid treatment at high temperatures and pressures (>100° C.) and/or concentrated acid pre-treatment, as described in "Cellulose to Ethanol": A General Review", P. C. Badger, in "Trends in New Crops and New Uses", J. Janick and A. Whipkey (Eds), ASHS Press, Alexandria Va., 2002, 17-21. Dilute acid processes are conducted at high temperature under pressure (for example, using 1% sulphuric acid at 237° C.). Concentrated acid processing typically starts with an initial acid concentration of 10% which is raised to 70% through dewatering at 100° C. and ambient pressure.

Because of the low yields and/or extreme conditions associated with these known processes, there remains the need for an improved method of hydrolysing cellulose by chemical means. Specifically, there is a need for a relatively rapid reaction which may be carried out under relatively mild conditions to give an adequately high conversion to sugars.

It is known that cellulose can be dissolved in certain ionic liquids. For example, U.S. Pat. No. 6,824,599 discloses that understood to include both cellulose itself and cellulose-containing material, either in raw or purified form. The cellulose that is to be hydrolysed may be either cellulose which has been refined to any desired degree, or it may be raw or partially-treated cellulosic material, such as cellulosic biomass or municipal waste. It may be used in any form that is amenable to being wetted by a liquid. For example, the cellulose may be present in, or derived from, wood (particularly, wood chips and wood pulp), cotton, rayon, cellulose acetate, paper, linters, grasses such as corn stover or switch grass, or bagasse (sugar cane residue).

The acid used in the process of the invention is a strong acid, having a pKa in water of less than 2, preferably less than 1, preferably 0 or less, at 25° C. An acid with a pKa of 0 is fully dissociated in water, and such acids are preferred for use in the present invention. The acids used in the invention are of the Brönsted (or protonic) type. Suitable acids include for example hydrogen halides, sulfuric acid, nitric acid, strong halocarboxylic acids, halosulfonic acids, tetrafluoroboric acid, heteropolyacids, aryl- and alkyl-sulfonic acids, and halogenated alkyl- and arylsulfonic acids. Examples of suitable acids include, for example, trifluoroacetic acid, p-toluenesulfonic acid, trifluoromethanesulfonic acid (triflic acid), trichloromethanesulfonic acid, hydrochloric acid, hydrobromic acid, hydriodic acid, tetrafluoroboric acid, and sulfuric acid. Preferred acids are sulfuric acid and hydrochloric acid, especially sulfuric acid.

The acid may be added in aqueous form, for example dilute aqueous form, or if desired may be anhydrous. Some water is needed in order for the hydrolysis reaction to occur as explained below, and this may either be present in the reaction mixture and/or added along with the acid. A mixture of acids may be used provided that at least one acid has the required acid strength, or the mixture has the required acid strength. In addition to the protonic acid, a Lewis acid may also be added to the reaction mixture if desired. Suitable Lewis acids include metal salts of strong protic acids (pKa less than about 0), in which the metal is for example lithium, potassium, magnesium, zinc, copper, aluminum, tin, antimony, iron, nickel or lanthanum. Suitable examples of such salts include, for example, metal halides, for example aluminum (III) chloride, gallium (III) chloride, indium (III) chloride and zinc (II) chloride; triflates, for example lithium triflate, sodium triflate, magnesium triflate, zinc triflate, aluminum triflate, tin(II) triflate, and copper(II) triflate; tetrafluoroborates, for example zinc (II) tetrafluoroborate, silver (II) tetrafluoroborate, iron (II) tetrafluoroborate, and nickel(II) tetrafluoroborate; and sulfonates, for example zinc p-toluenesulfonate.

Preferably, a catalytic amount of the acid is used. For example, the concentration of the acid in the reaction mixture may be from 0.1-10 wt %. If the reaction mixture before addition of the acid contains any basic material, some of the acid initially added will be neutralised, and sufficient acid needs to be added taking this into account.

The process of the invention is suitably carried out until a desired proportion of the cellulose is converted into water soluble derivatives. Suitably, the treatment with the acid proceeds for up to 96 hours, preferably less than 24 hours, more preferably less than 5 hours, and most preferably less than 1 hour.

The process of the invention may be carried out at any suitable temperature. Admixture of the cellulose with the ionic liquid must, of course, be carried out at a temperature at which the ionic liquid is in fact liquid. Subsequent reaction with the acid may if desired be accelerated by heating; for example, the reaction may be carried out at a temperature in the range 50 to 200° C., preferably 70 to 150° C., for example 90 to 95° C. Heating can be accomplished by any suitable method, for example using conventional thermal methods, microwave heating or employing other sources such as ultrasound or infrared radiation. Preferably the reaction is carried out under atmospheric pressure.

The ionic liquid used in the process of the invention is a compound that consists of cations and anions and that is in a liquid state at a temperature at or below 150° C., preferably at or below 100° C., for example in the range −100° C. to 150° C., preferably −10 to 100° C. It is necessary that the ionic liquid should be capable of dissolving at least some of the cellulose, or should be capable of solvating at least some of the cellulose. Preferably the ionic liquid selected is one in which the cellulose has at least some solubility. When the cellulose is used in the form of biomass, solvation generally leads to swelling of the biomass, and this may be a preferred mode of operation when treating biomass. Alternatively, an ionic liquid may be selected in which the cellulose is readily soluble. On admixture of the cellulose with the ionic liquid, conditions may be chosen such that the cellulose becomes solvated by the ionic liquid; substantially all of the cellulose dissolves to form a homogeneous solution; or some cellulose dissolves while some remains undissolved. Particularly in the latter case, residual solid material may if desired be removed from the solution of cellulose in the ionic liquid by any suitable method. Alternatively, the mixture may be used without further treatment. Suitably, an ionic liquid is selected in which simple solvation or dissolution takes place—i.e. solvation or dissolution without cellulose derivatisation. Naturally, the ionic liquid should be adequately inert in the presence of the strong acid used in the process of the invention; ionic liquids containing basic groups which would neutralise the acid are undesirable.

The anion of the ionic liquid must be sulfate, hydrogen sulfate or nitrate. Preferably the anion is sulfate or hydrogen sulfate. Most surprisingly, it has been found that the use of ionic liquids containing other anions such as carboxylates, which have previously been shown to dissolve cellulose, does not lead to the satisfactory hydrolysis of cellulose.

Preferred cations which may be present in ionic liquids for use in the method of the present invention are disclosed in U.S. Pat. No. 6,284,599. The cations of the ionic liquid are preferably cyclic, preferably containing an optionally substituted cation selected from pyridinium, pyridazinium, pyrimidinium, pyrazinium, imidazolium, pyrazolium, oxazolium, triazolium, thiazolium, piperidinium, pyrrolidinium, quinolinium and isoquinolinium, and preferably correspond in structure to a formula selected from the group consisting of:

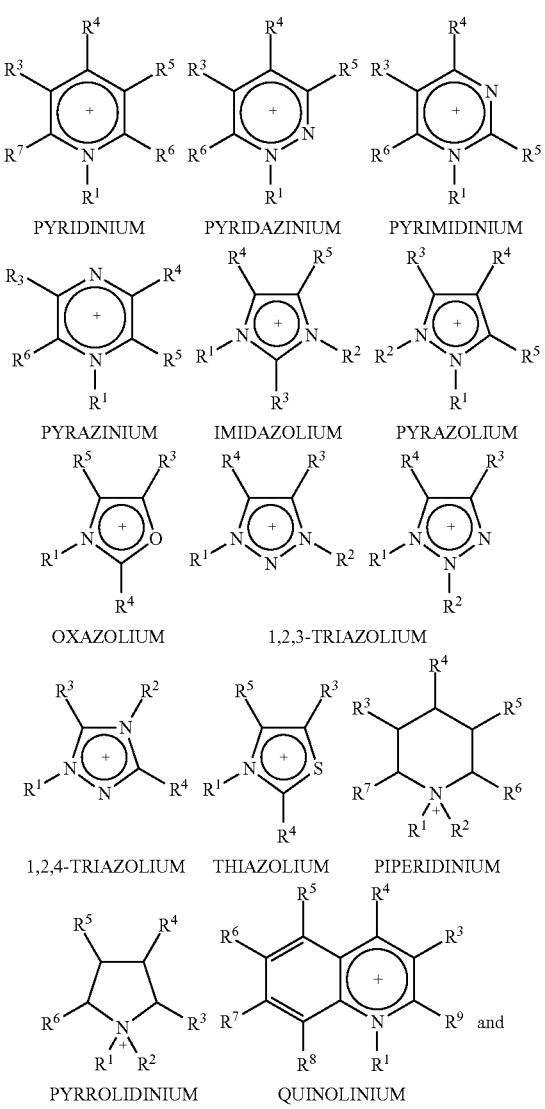

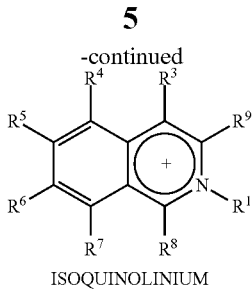

ISOQUINOLINIUM wherein $R^1$ and $R^2$ are independently a $C_1$-$C_6$ alkyl group or a $C_1$-$C_6$ alkoxyalkyl group, and $R^3$, $R^4$, $R^5$, $R^6$, $R^7$, $R^8$ and $R^9$ ($R^3$-$R^9$), when present, are independently selected from a hydrido, a $C_1$-$C_6$ alkyl, a $C_1$-$C_6$ alkoxyalkyl group or a $C_1$-$C_6$ alkoxy group. More preferably, both $R^1$ and $R^2$ groups are $C_1$-$C_4$ alkyl, with one preferably being methyl, and $R^3$-$R^9$, when present, are preferably hydrido. Exemplary $C_1$-$C_6$ alkyl groups include methyl, ethyl, propyl, iso-propyl, butyl, sec-butyl, iso-butyl, pentyl, iso-pentyl, hexyl, 2-ethylbutyl, 2-methylpentyl and the like. Corresponding $C_1$-$C_6$ alkoxy groups contain the above $C_1$-$C_6$ alkyl group bonded to an oxygen atom that is also bonded to the cation ring. An alkoxyalkyl group contains an ether group bonded to an alkyl group, and here contains a total of up to six carbon atoms. It is to be noted that there are two isomeric 1,2,3-triazoles. It is preferred that all R groups not required for cation formation be hydrido.

The phrase "when present" is used herein in regard to substituent R groups because not all cations have all of the numbered groups. All of the contemplated cations contain at least four R groups, although $R^2$ need not be present in all cations.

A cation that contains a single five-membered ring that is free of fusion to other ring structures is more preferred, for example, an imidazolium cation of Formula A is particularly preferred, wherein $R^1$, $R^2$, and $R^3$-$R^5$, are as defined before; preferably the anion of the ionic liquid is one of those given above, especially a halogen or pseudohalogen.

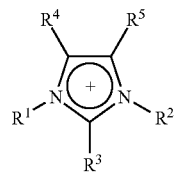

A

A 1,3-di-($C_1$-$C_6$ alkyl or $C_1$-$C_6$ alkoxyalkyl)-substituted-imidazolium ion is a more particularly preferred cation; i.e., an imidazolium cation wherein $R^3$-$R^5$ of Formula A are each hydrido, and $R^1$ and $R^2$ are independently each a $C_1$-$C_6$-alkyl group or a $C_1$-$C_6$ alkoxyalkyl group. More preferably still one of the 1,3-di-$C_1$-$C_6$ alkyl groups $R^1$ or $R^2$ is methyl.

A 1-($C_1$-$C_6$-alkyl)-3-(methyl)-imidazolium [$C_n$-mim, where n=1-6] cation is most preferred. A most preferred cation is illustrated by a compound that corresponds in structure to Formula B, below, wherein $R^3$-$R^5$ of Formula A are each hydrido and $R^1$ is a $C_1$-$C_6$ alkyl group or a $C_1$-$C_6$ alkoxyalkyl group.

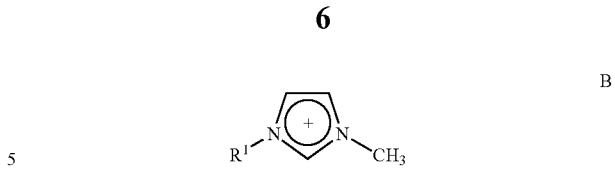

B

Also preferred are pyridinium cations analogous to the imidazolinium cations discussed above, for example 1-$C_{1-6}$ alkylpyridinium cations. Thus, especially preferred cations are a 1-methyl-3-$C_{1-6}$alkylimidazolium or a 1-$C_{1-6}$alkylpyridiniium cation. Preferably a $C_{1-6}$ alkyl group is a $C_{1-4}$ alkyl group, for example a methyl or ethyl group.

Typically, cellulose is admixed with the ionic liquid in an amount of at least 5% by weight, preferably in an amount of 5 to about 35% weight, for example 5 to 25% percent by weight, especially 10 to about 25% percent by weight.

Stoichiometrically, the hydrolysis reaction requires the presence of one mole equivalent of water for each monomer unit in the cellulose. Cellulose itself contains a certain amount of water, the exact amount depending upon the source and the physical form of the cellulose; usually, prepared cellulose contains at least 10-15% by weight of water. Further water is added to the reaction mixture if aqueous acid is used. However, excessively high amounts of water in the reaction mixture may result in either reduced solubility of the cellulose in the ionic liquid, and/or reduced conversion of cellulose to water-soluble hydrolysis products. Preferably the total water content of the reaction system is such that the weight ratio of water to cellulose is from 1:1 to 1:20, preferably from 1:5 to 1:15, especially about 1:10.

If desired, an additional co-solvent which is compatible with the ionic liquid may be present in the reaction mixture along with the cellulose and the ionic liquid, for example to modify the viscosity of the reaction mixture. Suitable solvents include non-basic polar solvents, for example dimethylsulfoxide, dimethylformamide and sulfolane.

As stated above, the cellulose may be either refined or derived directly from cellulosic biomass, municipal waste or other sources. The water-soluble products of the hydrolysis of cellulose include (a) water soluble oligosaccharides having 3 to 10 D-glucose units; (b) cellobiose; (c) monosaccharides such as glucose and fructose; and (d) glucose derivatives such as levoglucosan, levoglucosenone, levulinic acid, formic acid, 2-furfural, 5-hydroxymethyl-2-furfural, 5-methyl-2-furfural, 2,3-butanedione, glycolaldehyde, glyoxal, 2-furylhydroxymethylketone and pyruval. In general, the most desired products obtainable using the process of the invention are glucose and/or its water soluble oligomers.

When the conversion of cellulose to products has proceeded to the required extent, the reaction mixture may be worked up by any suitable method. For example, water or another solvent, for example an alcohol, e.g. ethanol, may be added to the reaction mixture in order to precipitate any residual cellulose or any insoluble hydrolysis products. Where the ionic liquid is hydrophilic and water is added, an aqueous solution of the ionic liquid and the water-soluble hydrolysis products may be produced. Preferably, the ionic liquid used in the process of the invention is at least partially recovered and reused in the process of the invention. If necessary, any solid material, for example comprising undissolved or unconverted cellulose and/or water insoluble cellulose hydrolysis products, may be separated by any suitable method, and if desired, recycled back to the start of the process.

Alternatively, the reaction mixture or any fraction thereof may be used directly in any subsequent step required to process the products of the reaction.

In a preferred embodiment of the process of the invention, subsequent processing of the products formed is carried out to produce lower alcohols, particularly ethanol, suitable for use as a biofuel. Thus, in a further embodiment, the invention provides a process for the preparation of one or more alcohols, which comprises admixing cellulose with an ionic liquid capable of solvating or dissolving at least some of the cellulose, said ionic liquid being a compound comprised solely of cations and anions and which exists in a liquid state at a temperature at or below 150° C., and in which the anions are selected from sulfate, hydrogen sulfate and nitrate; and treating the resulting solvate or solution with an acid in the presence of water, said acid having a pKa in water of less than 2 at 25° C., and converting at least part of the resulting product into one or more alcohols. The water-soluble cellulose hydrolysis products may for example be converted into alcohols by fermentation.

The following Examples illustrate the invention.

EXAMPLE 1

10 g of 1-ethyl-3-methylimidazolium sulfate ($Emim_2SO_4$) were placed in a round bottomed flask and heated to 100° C., upon which it melted. 0.25 ml of conc. $H_2SO_4$ was added dropwise through a syringe, after a few moments 0.5 g *Miscanthus* (milled to 0.5 mm) was added in two instalments and the stirring speed set to maximum in order to effect efficient wetting of the substrate. Samples were taken periodically and analysed by refractive index high performance liquid chromatography. The yield of water-soluble products having glucose end-groups was 18% after 60 mins.

EXAMPLE 2

The process of Example 1 was repeated except that 5 ml water were added to the reaction mixture using a syringe, 2 minutes after adding the *Miscanthus*. The yield of water-soluble products having glucose end-groups was 30% after 60 mins.

EXAMPLE 3

5 g of ethylpyridinium hydrogen sulfate were placed in a round bottomed flask and heated 15 to 100° C. 0.25 ml of conc. HCl was added dropwise through a syringe, after a few moments 0.25 g *Cortaderia* (milled to 0.5 mm) was added in two instalments and the stirring speed set to maximum in order to effect efficient wetting of the substrate. After 2 minutes, 5 ml water were added through a syringe. Samples were taken periodically and analysed by refractive index high performance liquid chromatography. The yield of water-soluble products having glucose end-groups was 22.5% after 5 mins.

EXAMPLE 4

The process of Example 3 was repeated except that the temperature used was 75° C. The yield of water-soluble products having glucose end-groups was 20% after 90 mins.

EXAMPLE 5 (COMPARATIVE)

0.25 g of fibrous cellulose were dissolved in 2 g of 1-ethyl-3-methylimidazolium acetate at 110° C. 0.3 mL of conc. HCl were added to this and the reaction mixture was sampled after 5, 15, 30, 90 and 180 minutes. No glucose products were detected by refractive index HPLC, or by DNS analysis.

EXAMPLE 6 (COMPARATIVE)

5 g of 1-ethyl-3-methylimidazolium bis(trifluoromethylsulfonyl)imide ($Emim.NTf_2$) were placed in a round bottomed flask and heated to 100° C., upon which it melted. 0.125 ml of conc. $H_2SO_4$ was added dropwise through a syringe, after a few moments 0.5 g *Miscanthus* (milled to 0.5 mm) was added in two instalments and the stirring speed set to maximum in order to effect efficient wetting of the substrate. Samples were taken periodically and analysed by refractive index high performance liquid chromatography. The yield of water-soluble products having glucose end-groups was extremely low, 0.6% after 60 mins. Repeating the experiment with the addition of 2 ml water 2 minutes after adding the *Miscanthus* increased the yield only marginally (to 0.7% after 60 minutes).

The invention claimed is:

1. A process for the preparation of water-soluble cellulose hydrolysis products, which comprises admixing cellulose with an ionic liquid capable of solvating or dissolving at least some of the cellulose, said ionic liquid being a compound comprised solely of cations and anions and which exists in a liquid state at a temperature at or below 150° C., and in which the anions are selected from sulfate, hydrogen sulfate and nitrate;

and treating the resulting solvate or solution with an acid in the presence of water, said acid having a pKa in water of less than 2 at 25° C.

2. A process as claimed in claim 1, in which said ionic liquid is one in which the cellulose has at least some solubility.

3. A process as claimed in either claim 1, in which the acid has a pKa in water of 0 or less at 25° C.

4. A process as claimed in either claim 1, in which the acid is selected from hydrogen halides, sulfuric acid, nitric acid, halocarboxylic acids, halosulfonic acids, tetrafluoroboric acid, heteropolyacids, aryl- and alkyl-sulfonic acids, and halogenated alkyl- and arylsulfonic acids.

5. A process as claimed in claim 4, in which the acid is trifluoroacetic acid, p-toluenesulfonic acid, trifluoromethanesulfonic acid, trichloromethanesulfonic acid, hydrochloric acid, hydrobromic acid, hydriodic acid, tetrafluoroboric acid, or sulfuric acid.

6. A process as claimed in claim 5, in which the acid is sulfuric acid or hydrochloric acid.

7. A process as claimed in claim 1, in which the reaction with the acid is carried out at a temperature in the range of from 50 to 200° C.

8. A process as claimed in claim 1, in which the cation of the ionic liquid is selected from pyridinium, pyridazinium, pyrim'dinium, pyrazinium, imidazoHum, pyrazoliurn, oxazolium, triazoHum, thiazolium, piperidinium, pyrrolidinium, quinolinium and isoquinolinium.

9. A process as claimed in claim 8, in which the cation of the ionic liquid has a structure 5 selected from the group consisting of:

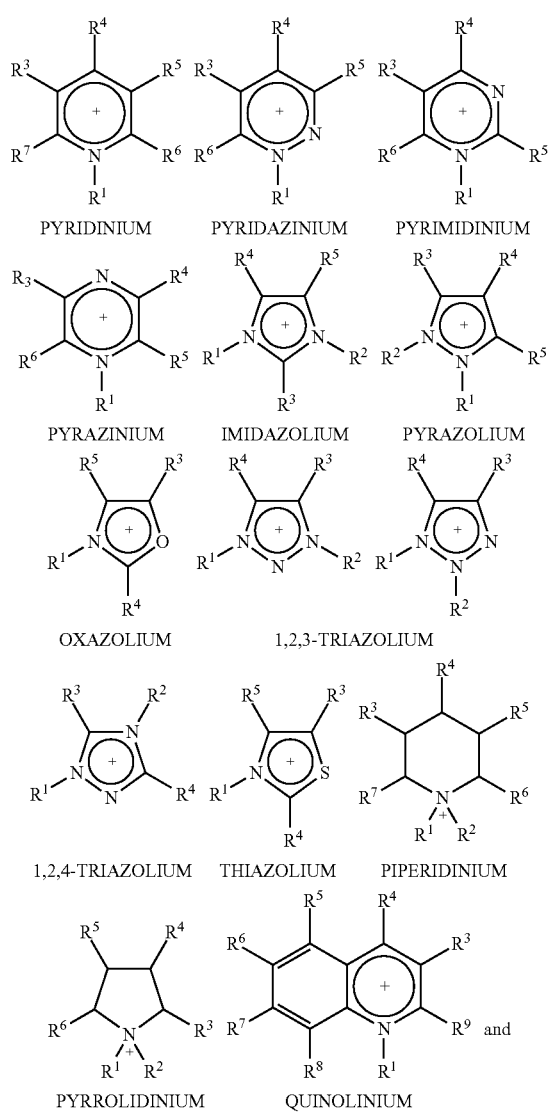

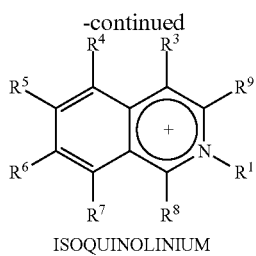

ISOQUINOLINIUM wherein $R^1$ and $R^2$ are independently a $C_1$-$C_6$ alkyl group or a $C_1$-$C_6$ alkoxyalkyl group, and $R^3$, $R^4$, $R^5$, $R^6$, $R^7$, $R^8$ and $R^9$ ($R^3$-$R^9$), when present, are independently selected from hydrido, $C_1$-$C_6$ alkyl, $C_1$-$C_6$ alkoxyalkyl or $C_1$-$C_6$ alkoxy.

10. A process as claimed in claim 9, in which in the cation of the ionic liquid, both $R^1$ and $R^2$ groups, when present, are $C_1$-$C_6$ alkyl, and $R^3$-$R^9$, when present, are hydrido.

11. A process as claimed in claim 9, in which the cation of the ionic liquid is an imidazolium cation or a pyridinium cation as shown in claim 9, wherein $R^1$-$R^7$, where present, are as defined in claim 9.

12. A process as claimed in claim 11, in which $R^3$-$R^7$, where present, are each hydrido, and $R^1$ and $R^2$ are independently each a $C_1$-$C_6$-alkyl group or a $C_1$-$C_6$ alkoxyalkyl group.

13. A process as claimed in claim 12, in which the cation is a 1-methyl-3-$C_{1-6}$ealkylimidazolium or a cation.

14. A process as claimed in claim 1, in which the anion of the ionic liquid is sulfate or hydrogen sulfate.

15. A process as claimed in claim 1, in which the cellulose is admixed with the ionic liquid in an amount of from 5 to 35% weight.

16. A process as claimed in claim 1, in which the water content of the reaction system is such that the weight ratio of water to cellulose is from 1:1 to 1:20.

17. A process as claimed in claim 16, in which the water content of the reaction system is such that the weight ratio of water to cellulose is from 1:5 to 1:15.

18. A process for the preparation of one or more alcohols, which comprises carrying out a process as claimed in claim 1, and converting at least part of the resulting product into one or more alcohols.

\* \* \* \* \*